United States Patent [19]
Herbots et al.

[11] Patent Number: 6,030,933
[45] Date of Patent: Feb. 29, 2000

[54] DETERGENT COMPOSITIONS COMPRISING IMMOBILIZED ENZYMES

[75] Inventors: Ivan Maurice Alfons Jan Herbots, Hollegat; Madeleine Petronella Jansen, Heilige Geeststraat; Andre Cesar Baeck, Putsesteenweg; Jean Wevers, Heide, all of Belgium

[73] Assignee: The Procter & Gamble Company, Cincinnati, Ohio

[21] Appl. No.: 09/101,073

[22] PCT Filed: Dec. 29, 1995

[86] PCT No.: PCT/US95/17039

§ 371 Date: Jun. 29, 1998

§ 102(e) Date: Jun. 29, 1998

[87] PCT Pub. No.: WO97/24421

PCT Pub. Date: Jul. 10, 1997

[51] Int. Cl.⁷ .............................. C11D 7/42; C11D 3/386; C12S 11/00; D06L 3/37
[52] U.S. Cl. ..................... 510/392; 510/276; 510/284; 510/300; 510/321; 510/337; 510/349; 510/360; 510/393; 510/405; 510/446; 510/475; 510/515; 510/527; 510/530; 510/531; 134/42
[58] Field of Search ................................... 510/276, 300, 510/320, 321, 337, 349, 392, 405, 446, 475, 515, 527, 530, 531, 284, 393, 360; 134/42

[56] References Cited

U.S. PATENT DOCUMENTS

| | | | |
|---|---|---|---|
| 4,088,538 | 5/1978 | Schneider | 435/94 |
| 4,532,212 | 7/1985 | Odell | 435/197 |
| 4,600,693 | 7/1986 | Kindle et al. | 435/176 |
| 4,640,835 | 2/1987 | Shimizu et al. | 424/94 |
| 4,711,739 | 12/1987 | Kandathil | 510/284 |
| 4,844,897 | 7/1989 | Maeda et al. | 424/94.3 |
| 4,885,207 | 12/1989 | Johnson et al. | 428/403 |
| 4,908,150 | 3/1990 | Hessel et al. | 510/393 |
| 4,910,135 | 3/1990 | Tischer et al. | 435/28 |
| 4,935,465 | 6/1990 | Garman | 525/54.1 |
| 5,080,891 | 1/1992 | Saifer et al. | 424/78.3 |
| 5,133,968 | 7/1992 | Nakayama et al. | 424/401 |
| 5,281,356 | 1/1994 | Tsaur et al. | 252/174.13 |
| 5,281,357 | 1/1994 | Morgan et al. | 252/174.13 |
| 5,298,410 | 3/1994 | Phillips et al. | 435/188 |
| 5,458,810 | 10/1995 | Fredj et al. | 252/542 |
| 5,532,150 | 7/1996 | Snow et al. | 435/188 |
| 5,868,868 | 2/1999 | Park et al. | 134/42 |
| 5,888,950 | 3/1999 | Potini et al. | 510/113 |

FOREIGN PATENT DOCUMENTS

| | | | |
|---|---|---|---|
| 0 223221 | 5/1987 | European Pat. Off. | C12N 11/10 |
| 0 223479 | 5/1987 | European Pat. Off. | A61L 2/18 |
| 0 319957 | 6/1989 | European Pat. Off. | C08J 7/12 |
| 1-285188 | 11/1989 | Japan | C11D 3/38 |
| 6-240297 | 8/1994 | Japan | C11D 7/42 |
| 1297316 | 11/1972 | United Kingdom | C07G 7/02 |
| 1 353 317 | 5/1974 | United Kingdom | C07G 7/02 |
| WO 91/17243 | 11/1991 | WIPO | |
| WO 93/15189 | 8/1993 | WIPO | C12N 9/96 |
| WO 96/17929 | 6/1996 | WIPO | C12N 9/96 |
| WO 96/40791 | 12/1996 | WIPO | C07K 17/08 |
| WO 96/40792 | 12/1996 | WIPO | C07K 17/08 |

OTHER PUBLICATIONS

Prikladnaya Biokhimiya i Mikrobiologiya, vol. 14, No. 5, pp. 703–708 (1983) No Month Given.

Abuchowski, A., et al., "Cancer Therapy with Chemically Modified Enzymes. I. Antitumor Properties of Polyethylene Glycol–Asparaginase Conjugates", Cancer Biochem Biophys, vol. 7, pp. 175–186 (1984) No Month Given.

Bückmann, A.F., et al., "Functionalization of Poly(ethylene glycol) and Monomethoxy–Poly(ethylene glycol)", Makromol. Chem., vol. 182, pp. 1379–1384 (1981) No Month Given.

Caliceti, P., et al., "Active Site Protection of Proteolytic Enzymes by Poly(ethylene glycol) Surface Modification", J. Bioactive and Compatible Polymers, vol. 8, pp. 41–50 (Jan. 1993).

Delgado, C., et al., "The Uses and Properties of PEG–Linked Proteins", Critical Reviews in Therapeutic Drug Carrier Systems, vol. 9, No. 3,4, pp. 249–304 (1992) No Month Given.

Francis, G.E., et al., "PEG–Modified Proteins", Stability of Protein Pharmaceuticals, Part B: In Vivo Pathways of Degradation and Strategies for Protein Stabilization, Ed. Ahern/Manning, Plenum Press, NY, Chptr. 8, pp. 235–263 (1992) No Month Given.

Hershfield, M.S., et al., "Use of Site–directed Mutagenesis to Enhance the Epitope–shielding Effect of Covalent Modification of Proteins with Polyethylene Glycol", Proc. Natl. Acad. Sci. USA, vol. 88, pp. 7185–7189 (Aug. 1991).

Katre, N.V., "The Conjugation of Proteins with Polyethylene Glycol and Other Polymers, Altering properties of proteins to enhance their therapeutic potential", Advanced Drug Delivery Reviews, vol. 10, pp. 91–114 (1993) No Month Given.

(List continued on next page.)

*Primary Examiner*—Yogendra Gupta
*Assistant Examiner*—Brian P. Mruk
*Attorney, Agent, or Firm*—Kelly L. McDow-Dunham; C. Brant Cook; Kim W. Zerby

[57] ABSTRACT

The present invention relates to detergent compositions comprising one or more enzymes which are immobilized by a covalent binding on an activated polymer. Such enzymes are preferably bound to the activated polymer via a spacer molecule. The enzymes are selected from a variety of enzymes including, for example, cellulases, hemicellulases, peroxidases, proteases, glucoamylases, amylases, lipases, cutinases, pectinases, reductases, oxidases, phenoloxidases, lipoxygenases, laccases, ligninases, pullulanases, xylanases, tannases, pentosanases, manlanases, β-glucanases, arabinosidases, and mixtures thereof. The polymer is selected from a variety of polymers. A preferred polymer for use in the present invention is polyethylene glycol.

17 Claims, No Drawings

OTHER PUBLICATIONS

Khan, S.A., et al., "Polyethylene Glycol–modified Subtilisin Forms Microparticulate Suspensions in Organic Solvents", Enzyme Microb. Technol., vol. 14, pp. 96–100 (Feb. 1992).

Mishra, C., et al., "Immobilization of *Pencillium funiculosum* Cellulase on a Soluble Polymer", Enzyme Microb. Technol., vol. 5, pp. 342–344 (Sep. 1983).

Nishimura, H., et al., "Improved Modification of Yeast Uricase with Polyethylene Glycol, Accompanied with Non-immunoreativity Towards Anti–Uricase Serum and High Enzymic Activity", Enzyme, vol. 26, pp. 49–53 (1981) No Month Given.

Nucci, M.L., et al., "Immunogenicity of Polyethylene Glycol–modified Superoxide Dismutase and Catalase", J. Free Radicals in Biology & Medicine, vol. 2, pp. 321–325 (1986) No Month Given.

Nucci, M.L., et al., "The Therapeutic Value of Poly(ethylene glycol)–modified Proteins", Advanced Drug Delivery Reviews, vol. 6, pp. 133–151 (1991) No Month Given.

Savoca, K.V., et al., "Preparation of a Non–immunogenic Arginase by the Covalent Attachment of Polyethylene Glycol", Biochimica et Biophysica Acta, vol. 578, pp. 47–53 (1979) No Month Given.

Wongkhalaung, C., et al., "Cellulase Immobilized on a Soluble Polymer", Appl Microbiol Biotechnol, vol. 21, pp. 37–41 (1985) No Month Given.

DETERGENT COMPOSITIONS COMPRISING IMMOBILIZED ENZYMES

FIELD OF THE INVENTION

The present invention relates to detergent compositions comprising an enzyme which is immobilized on an activated polymer.

BACKGROUND OF THE INVENTION

Over the years, a number of enzyme products have been developed for incorporation into detergents. Unfortunately, many commercially prepared enzyme-based products have certain drawbacks. Enzyme-based products are often difficult to handle, may cause an irritating dust, may be incompatible with other detergent ingredients, and may deteriorate in the presence of moisture. In addition, it is well known in the art that enzyme deactivation occurs in aqueous detergent compositions containing enzymes.

Consequently, there is a standing desire to prepare enzyme products suitable for detergents which overcome the above drawbacks.

It has now been found that one or more enzymes immobilized on an activated polymer are very suitable for incorporation into detergent compositions. The inclusion of such immobilized enzymes in a detergent composition provide an improved thermal stability, especially in liquid detergents. In addition, an improved resistance of said immobilized enzymes occurs against premature proteolysis due to protease. Furthermore, a better controlled enzymatic activity on fabrics can be achieved using said immobilized enzymes on an activated polymer in detergents.

In addition, it has been surprisingly found that utilization of said immobilized enzymes in detergents also delivers an important whiteness maintenance and a reduced potential to generate improved odor characteristics.

It is known in the art that enzymes can be attached to polymers. In Applied Microbiology and Biotechnology (1985), 21:37–41 is disclosed the immobilization of Aspergillus niger cellulase on cyanogen bromide activated dextran of varying molecular weights. In Enzyme Microb. Technology, 1983, Vol 5, 342–344 is disclosed the immobilization of three cellulase components of Penicillium funiculosum on a soluble, high molecular weight polymer (polyvinyl alcohol), using carbodiimide. In Prikladnaya Biokhimiya i Mikrobiologiya, Vol 14, No. 5, pp703–708 is described the covalent immobilization of lipase and amylase on soluble and insoluble copolymers of N-vinylpyrrolidone with glycidyl acrylate and glycidyl methacrylate. In the Japanese patent application J06240297 of Toray Industries is disclosed a cleaning agent containing enzymes immobilized on water-soluble organic high molecular weight polymers. The agent is prepared by mixing the enzymes and a polymer, preferably a methyl vinyl ether-maleic anhydride copolymer. Using this method the enzyme loosely immobilized on the polymer can easily be washed/rinsed away from the polymer.

However, nowhere is disclosed the benefit of using enzymes immobilized via a covalent binding on activated polymeric supports in detergent compositions.

SUMMARY OF THE INVENTION

The current invention relates to detergent compositions comprising one or more enzymes which are immobilized by a covalent binding on an activated polymeric support. Preferably the polymeric support is polyethylene glycol.

DETAILED DESCRIPTION OF THE INVENTION

An essential component of the detergent compositions of the invention is that one or more enzymes are immobilized on an activated polymer. The immobilization is achieved by a covalent binding of said enzyme(s) to the carrier.

The immobilization of one or more enzymes on activated polymers compatible with detergents and especially with liquid detergent matrices surprisingly offers the following advantages:

improved thermal stability of the immobilized enzymes, especially in liquid detergent;

improved resistance of the immobilized enzyme(s) against premature proteolysis due to protease, and especially in liquid detergents;

reduced deposition of the immobilized enzyme(s) on fabrics due to increased rinse-away. Hence better whiteness maintenance; reduced potential to generate fabric malodor due to enzymatic activity (e.g. lipase on perspiration) and due to microbial growth on fabrics;

an improved antigenicity profile of the enzyme protein;

a reduced potential tensile strength loss related to enzymatic activity on fabrics. It should be noted, however, strength loss of fabric is also an unavoidable result of mechanical action due to use/wearing and may further result from damage by a bleaching component, especially if the fabric is contaminated by metallic particles.

Said advantages can be achieved by structurally modifying the enzyme without affecting the enzyme performance profile in the detergent solution by the covalent immobilization of one or more enzymes to an activated polymeric support with or without spacer molecule. The covalent enzyme immobilization is achieved by applying the conventional chemistry.

This achieved structural modification of the enzyme is stable in a detergent and in the wash solution. Encapsulated or prilled enzymes without the structural modification of the enzyme are released in the wash solution and do not deliver the advantages associated with the structurally modified enzymes. The present invention has proven to be particularly useful for enzymes which provide cleaning performance and/or fabric care benefits.

Enzymes

The enzyme according to the present invention includes enzymes selected from cellulases, hemicellulases, peroxidases, proteases, gluco-amylases, amylases, lipases, cutinases, pectinases, reductases, oxidases, phenoloxidases, laccases, lipoxygenases, ligninases, pullulanases, xylanases, tannases, pentosanases, malanases, β-glucanases, arabinosidases or mixtures thereof.

A preferred combination is a cleaning composition having cocktail of conventional applicable enzymes like protease, amylase, lipase, cutinase and/or cellulase covalently bound to a polymer.

The cellulases usable in the present invention include both bacterial or fungal cellulase. Preferably, they will have a pH optimum of between 5 and 9.5. Suitable cellulases are disclosed in U.S. Pat. No. 4,435,307, Barbesgoard et al, which discloses fungal cellulase produced from Humicola insolens. Suitable cellulases are also disclosed in GB-A-2.075.028; GB-A-2.095.275 and DE-OS-2.247.832.

Examples of cellulase components which may be usable in the present invention are:

A cellobiohydrolase component which is immunoreactive with an antibody raised against a highly purified ~70 kD cellobiohydrolase (EC 3.2.1.91) derived from Humicola insolens, DSM 1800, or which is a homologue or derivative of the ~70 kD cellobiohydrolase exhibiting cellulase activity, or an endoglucanase component which is immunoreactive with an antibody raised against a highly purified ~50 kD endoglucanase derived from Humicola insolens, DSM 1800, or which is a homologue or derivative of the ~50 kD endoglucanase exhibiting cellulase activity; a preferred endoglucanase component has the amino acid sequence disclosed in PCT Patent Application No. WO91/17244, or an endoglucanase component which is immunoreactive with an antibody raised against a highly purified ~50 kD (apparent molecular weight, the amino acid composition corresponds to 45 kD with 2n glycosylation sites) endoglucanase derived from Fusarium oxysporum, DSM 2672, or which is a homologue or derivative of the ~50 kD endoglucanase exhibiting cellulase activity; a preferred endoglucanase component has the amino acid sequence disclosed in PCT Patent Application No. WO91/17244, or any of the cellulases disclosed in the published European Patent Application No. EP-A2-271 004, the cellulases having a non-degrading index (NDI) of not less than 500 and being alkalophilic cellulases having an optimum pH not less than 7 or whose relative activity at a pH of not less than 8 is 50% or over of the activity under optimum conditions when carboxy methyl cellulose (CMC) is used as a substrate, or an endoglucanase component which is immunoreactive with an antibody raised against a highly purified ~43 kD endoglucanase derived from Humicola insolens, DSM 1800, or which is a homologue or derivative of the ~43 kD endoglucanase exhibiting cellulase activity; a preferred endoglucanase component has the amino acid sequence disclosed in PCT Patent Application No. WO 91/17243, or an endoglucanase component which is immunoreactive with an antibody raised against a highly purified ~60 kD endoglucanase derived from Bacillus lautus, NCIMB 40250, or which is a homologue or derivative of the ~60 kD endoglucanase exhibiting cellulase activity; a preferred endoglucanase component has the amino acid sequence disclosed in PCT Patent Application No. WO 91/10732.

Especially suitable cellulases are the cellulases having color care benefits. Examples of such cellulases are cellulases described in European patent application No. 91202879.2, filed Nov. 6, 1991 (Novo).

Peroxidase enzymes are used in combination with oxygen sources, e.g. percarbonate, perborate, persulfate, hydrogen peroxide, etc. They are used for "solution bleaching", i.e. to prevent transfer of dyes or pigments removed from substrates during wash operations to other substrates in the wash solution. Peroxidase enzymes are known in the art, and include, for example, horseradish peroxidase, ligninase, and haloperoxidase such as chloro- and bromo-peroxidase. Peroxidase-containing detergent compositions are disclosed, for example, in PCT International Application WO 89/099813 and in European Patent application EP No. 91202882.6, filed on Nov. 6, 1991.

Said cellulases and/or peroxidases are normally incorporated in the detergent composition at levels from 0.0001% to 2% of active enzyme by weight of the detergent composition.

Preferred commercially available protease enzymes include those sold under the tradenames Alcalase, Savinase, Primase, Durazym, and Esperase by Novo Nordisk A/S (Denmark), those sold under the tradename Maxatase, Maxacal and Maxapem by Gist-Brocades, those sold by Genencor International, and those sold under the tradename Opticlean and Optimase by Solvay Enzymes. Also proteases described in our co-pending application U.S. Ser. No. 08/136,797 can be included in the detergent composition of the invention. Protease enzyme may be incorporated into the compositions in accordance with the invention at a level of from 0.0001% to 2% active enzyme by weight of the composition.

Other preferred enzymes that can be included in the detergent compositions of the present invention include lipases. Suitable lipase enzymes for detergent usage include those produced by microorganisms of the Pseudomonas group, such as Pseudomonas stutzeri ATCC 19.154, as disclosed in British Patent 1,372,034. Suitable lipases include those which show a positive immunological cross-reaction with the antibody of the lipase, produced by the microorganism *Pseudomonas fluorescent* IAM 1057. This lipase is available from Amano Pharmaceutical Co. Ltd., Nagoya, Japan, under the trade name Lipase P "Amano," hereinafter referred to as "Amano-P". Especially suitable lipases are lipases such as M1 Lipase$^R$ and Lipomax$^R$ (Gist-Brocades) and Lipolase$^R$ (Novo) which have found to be very effective when used in combination with the compositions of the present invention. Also suitable are cutinases [EC 3.1.1.50] which can be considered as a special kind of lipase, namely lipases which do not require interfacial activation. Addition of cutinases to detergent compositions have been described in e.g. WO-A-88/09367 (Genencor).

The lipases and/or cutinases are normally incorporated in the detergent composition at levels from 0.0001% to 2% of active enzyme by weight of the detergent composition.

Amylases ($\alpha$ and/or $\beta$) can be included for removal of carbohydrate-based stains. Suitable amylases are Termamyl$^R$ (Novo Nordisk), Fungamyl$^R$ and BAN$^R$ (Novo Nordisk). The above-mentioned enzymes may be of any suitable origin, such as vegetable, animal, bacterial, fungal and yeast origin.

Said enzymes are normally incorporated in the detergent composition at levels from 0.0001% to 2% of active enzyme by weight of the detergent composition.

Activated Polymer

The activated polymer as defined herein are polymers which are preferably mono-functionalized with chemically reactive groups which are capable to covalently react with specific amino acid residues of a protein, e.g. of an enzyme. Activation chemistry is known in the art by skilled persons. The activated polymer forms a stable and water-soluble complex with the protein.

The polymer can be either soluble in water or in liquid detergent or be insoluble in water. The molecular weight range is from 0.5 kD up to 5000 kD. Examples are polyvinyl alcohols; polyvinyl pyrrolidone; polyacryl amides; poly acrylates; alpha-hydroxy poly acrylates; polyamine N-oxide polymers; copolymers of N-vinylpyrrolidone and N-vinylimidazole, polyvinyloxa-zolidones and polyvinylimidazoles or mixtures thereof; copolymers of PVA or PVP; block polymers of ethylene oxide and propylene oxide; poly saccharides, e.g. cellulose; substituted celluloses; cyclodextrin; dextrans; agarose; proteins; collagen; poly aspartate. A preferred polymer is the poly ethylene glycol with molecular weights 5 kD upto 20 kD. The molar ratio of activated polymer to enzyme is from 0.5:1 to 100:1. Preferred molar ratio of activated polymer to cellulase is 5:1 to 60:1. Preferably, the polymer has a water solubility of at least $7.10^{-10}$ Mol/l.

Immobilization Techniques

Immobilization techniques are all conventional enzyme immobilization methods known in the art. These techniques include e.g. coupling of the enzyme to the polymer via cyanogen bromide or cyanogen chloride activation; via oxirane groups and other epoxide activated polymers; via divinylsulfone groups introduction; via benzoquinone reaction; by thiol-disulfide interchange with activated thiolated polysaccharide; via activated halogens induced in hydroxylic polymers; via azide formation with polyacrylamide; via azo-coupling to silanized carriers and sofort. Also bifunctional reagent are useful. Activated polymers include nucleophilic PEGs, (e.g. PEG thiol) carboxyl PEGs (e.g. PEG succinate, carboxymethylated PEG, PEG propionic acid, PEG aminoacids), electrophillically activated PEGs (e.g. PEG succinimidyl succinate, succinimidyl derivatives of PEG propionic acid, active esters of amino acid PEGs, PEG oxycarbonylimidazole, PEG nitrophenol carbonate, PEG tresylate, PEG glycidyl ether, PEG aldehyde), heterofunctional PEGs, Vinyl Derivatives (e.g. allyl PEG, PEG (metha)acrylate), PEG silanes. These activated polymers are available from Shearwater Polymers Inc. The enzyme is immobilized either directly to the polymer or via a spacer molecule. The immobilization is single-point or multi-point attachment.

In order to retain enzyme activity after covalent immobilization on polymer(s), a so-called active site protection of said enzyme is carried out prior to said covalent immobilization with cellobiose in case a cellulase is used or appropriate substrates for other enzymes. The covalent immobilization of the enzyme to the activated polymeric support can be achieved with or without a spacer molecule. The spacer molecule can be any monomeric or polymeric substance at minimum di-functionalized with chemically reactive groups which are capable to covalently react with specific amino acid residues of a protein, e.g. of an enzyme. The di-functional activated polymer cross links the proteins and forms a stable and water soluble compound with the protein.

The modified enzyme and the activated polymer is stable in normal detergent conditions as encountered in a conventional laundry process. The covalently bound polymer-enzyme essentially does not decompose and does not release more than 5% of any of the starting components of the modified enzyme when exposed to diluted wash solution up to pH11, at solution temperatures up to 90° C. and for at least 30 minutes. This in contrast to complexes formed by adsorption and aggregation phenomena of the enzyme protein to a soluble or insoluble carrier without activation where dynamic equilibria, affected by the laundry conditions, govern the complex stability in solution. In such aggregation- and adsorption complex, the major part of the immobilized enzyme can be released depending on the laundry conditions.

Detergent Components

The detergent compositions of the invention may also contain additional detergent components. The precise nature of these additional components, and levels of incorporation thereof will depend on the physical form of the composition, and the nature of the cleaning operation for which it is to be used.

The compositions of the invention may for example, be formulated as hand and machine laundry detergent compositions including laundry additive compositions and compositions suitable for use in the pretreatment of stained fabrics, rinse added fabric softener compositions, and compositions for use in general household hard surface cleaning operations.

When formulated as compositions suitable for use in a machine washing method, the compositions of the invention preferably contain both a surfactant and a builder compound and additionally one or more detergent components preferably selected from organic polymeric compounds, bleaching agents, additional enzymes, suds suppressors, dispersants, soil suspension and anti-redeposition agents and corrosion inhibitors. Laundry compositions can also contain softening agents, as additional detergent components.

If needed the density of the laundry detergent compositions herein ranges from 550 to 1000 g/liter, preferably 600 to 950 g/liter of composition measured at 20° C.

The "compact" form of the compositions herein is best reflected by density and, in terms of composition, by the amount of inorganic filler salt; inorganic filler salts are conventional ingredients of detergent compositions in powder form; in conventional detergent compositions, the filler salts are present in substantial amounts, typically 17–35% by weight of the total composition.

In the compact compositions, the filler salt is present in amounts not exceeding 15% of the total composition, preferably not exceeding 10%, most preferably not exceeding 5% by weight of the composition.

The inorganic filler salts, such as meant in the present compositions are selected from the alkali and alkaline-earth-metal salts of sulphates and chlorides.

A preferred filler salt is sodium sulphate.

Surfactant System

The detergent compositions according to the present invention comprise a surfactant system wherein the surfactant can be selected from nonionic and/or anionic and/or cationic and/or ampholytic and/or zwitterionic and/or semi-polar surfactants.

The surfactant is typically present at a level of from 0.1% to 60% by weight. More preferred levels of incorporation are 1% to 35% by weight of laundry and rinse added fabric softener compositions in accord with the invention.

The surfactant is preferably formulated to be compatible with enzyme components present in the composition. In liquid or gel compositions the surfactant is most preferably formulated such that it promotes, or at least does not degrade, the stability of any enzyme in these compositions.

Preferred non-alkylbenzene sulfonate surfactant systems to be used according to the present invention comprise as a surfactant one or more of the nonionic and/or anionic surfactants described herein.

Polyethylene, polypropylene, and polybutylene oxide condensates of alkyl phenols are suitable for use as the nonionic surfactant of the surfactant systems of the present invention, with the polyethylene oxide condensates being preferred. These compounds include the condensation products of alkyl phenols having an alkyl group containing from about 6 to about 14 carbon atoms, preferably from about 8 to about 14 carbon atoms, in either a straight-chain or branched-chain configuration with the alkylene oxide. In a preferred embodiment, the ethylene oxide is present in an amount equal to from about 2 to about 25 moles, more preferably from about 3 to about 15 moles, of ethylene oxide per mole of alkyl phenol. Commercially available nonionic surfactants of this type include Igepal™ CO-630, marketed by the GAF Corporation; and Triton™ X-45, X-114, X-100 and X-102, all marketed by the Rohm & Haas Company.

These surfactants are commonly referred to as alkylphenol alkoxylates (e.g., alkyl phenol ethoxylates).

The condensation products of primary and secondary aliphatic alcohols with from about 1 to about 25 moles of ethylene oxide are suitable for use as the nonionic surfactant of the nonionic surfactant systems of the present invention. The alkyl chain of the aliphatic alcohol can either be straight or branched, primary or secondary, and generally contains from about 8 to about 22 carbon atoms. Preferred are the condensation products of alcohols having an alkyl group containing from about 8 to about 20 carbon atoms, more preferably from about 10 to about 18 carbon atoms, with from about 2 to about 10 moles of ethylene oxide per mole of alcohol. About 2 to about 7 moles of ethylene oxide and most preferably from 2 to 5 moles of ethylene oxide per mole of alcohol are present in said condensation products. Examples of commercially available nonionic surfactants of this type include Tergitol™ 15-S-9 (the condensation product of $C_{11}$–$C_{15}$ linear alcohol with 9 moles ethylene oxide), Tergitol™ 24-L-6 NMW (the condensation product of $C_{12}$–$C_{14}$ primary alcohol with 6 moles ethylene oxide with a narrow molecular weight distribution), both marketed by Union Carbide Corporation; Neodol™ 45-9 (the condensation product of $C_{14}$–$C_{15}$ linear alcohol with 9 moles of ethylene oxide), Neodol™ 23-3 (the condensation product of $C_{12}$–$C_{13}$ linear alcohol with 3.0 moles of ethylene oxide), Neodol™ 45-7 (the condensation product of $C_{14}$–$C_{15}$ linear alcohol with 7 moles of ethylene oxide), Neodol™ 45-5 (the condensation product of $C_{14}$–$C_{15}$ linear alcohol with 5 moles of ethylene oxide) marketed by Shell Chemical Company, Kyro™ EOB (the condensation product of $C_{13}$–$C_{15}$ alcohol with 9 moles ethylene oxide), marketed by The Procter & Gamble Company, and Genapol LA 050 (the condensation product of $C_{12}$–$C_{14}$ alcohol with 5 moles of ethylene oxide) marketed by Hoechst. Preferred range of HLB in these products is from 8–11 and most preferred from 8–10.

Also useful as the nonionic surfactant of the surfactant systems of the present invention are the alkylpolysaccharides disclosed in U.S. Pat. No. 4,565,647, Llenado, issued Jan. 21, 1986, having a hydrophobic group containing from about 6 to about 30 carbon atoms, preferably from about 10 to about 16 carbon atoms and a polysaccharide, e.g. a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties (optionally the hydrophobic group is attached at the 2-, 3-, 4-, etc. positions thus giving a glucose or galactose as opposed to a glucoside or galactoside). The intersaccharide bonds can be, e.g. between the one position of the additional saccharide units and the 2-, 3-, 4-, and/or 6-positions on the preceding saccharide units. The preferred alkylpolyglycosides have the formula

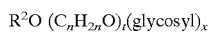

$R^2O\ (C_nH_{2n}O)_t(\text{glycosyl})_x$ wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominately the 2-position.

The condensation products of ethylene oxide with a hydrophobic base formed by the condensation of propylene oxide with propylene glycol are also suitable for use as the additional nonionic surfactant systems of the present invention. The hydrophobic portion of these compounds will preferably have a molecular weight of from about 1500 to about 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially-available Pluronic™ surfactants, marketed by BASF.

Also suitable for use as the nonionic surfactant of the nonionic surfactant system of the present invention, are the condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic™ compounds, marketed by BASF.

Preferred for use as the nonionic surfactant of the surfactant systems of the present invention are polyethylene oxide condensates of alkyl phenols, condensation products of primary and secondary aliphatic alcohols with from about 1 to about 25 moles of ethylene oxide, alkylpolysaccharides, and mixtures thereof. Most preferred are $C_8$–$C_{14}$ alkyl phenol ethoxylates having from 3 to 15 ethoxy groups and $C_8$–$C_{18}$ alcohol ethoxylates (preferably $C_{10}$ avg.) having from 2 to 10 ethoxy groups, and mixtures thereof.

Highly preferred nonionic surfactants are polyhydroxy fatty acid amide surfactants of the formula

wherein $R^1$ is H, or $R^1$ is $C_{1-4}$ hydrocarbyl, 2-hydroxy ethyl, 2-hydroxy propyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Preferably, $R^1$ is methyl, $R^2$ is a straight $C_{11-15}$ alkyl or $C_{16-18}$ alkyl or alkenyl chain such as coconut alkyl or mixtures thereof, and Z is derived from a reducing sugar such as glucose, fructose, maltose, lactose, in a reductive amination reaction.

When included in such laundry detergent compositions, the nonionic surfactant systems of the present invention act to improve the greasy/oily stain removal properties of such laundry detergent compositions across a broad range of laundry conditions.

Highly preferred anionic surfactants include alkyl alkoxylated sulfate surfactants hereof are water soluble salts or acids of the formula RO(A)$_m$SO3M wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydroxyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein, Specific examples of substituted ammonium cations include methyl-, dimethyl, trimethyl-ammonium cations and quaternary ammonium cations such as tetramethyl-ammonium and dimethyl piperdinium cations and those derived from alkylamines such as ethylamine, diethylamine, triethylamine, mixtures thereof, and the like. Exemplary surfactants are $C_{12}$–$C_{18}$ alkyl polyethoxylate (1.0) sulfate ($C_{12}$–$C_{18}$E(1.0)M), $C_{12}$–$C_{18}$ alkyl polyethoxylate (2.25) sulfate ($C_{12}$–$C_{18}$E(2.25)M), $C_{12}$–$C_{18}$ alkyl polyethoxylate (3.0) sulfate ($C_{12}$–$C_{18}$E(3.0)M), and $C_{12}$–$C_{18}$ alkyl polyethoxylate (4.0) sulfate ($C_{12}$–$C_{18}$E(4.0)M), wherein M is conveniently selected from sodium and potassium.

Suitable anionic surfactants to be used are alkyl ester sulfonate surfactants including linear esters of $C_8$–$C_{20}$ carboxylic acids (i.e., fatty acids) which are sulfonated with gaseous $SO_3$ according to "The Journal of the American Oil Chemists Society", 52 (1975), pp. 323–329. Suitable starting materials would include natural fatty substances as derived from tallow, palm oil, etc.

The preferred alkyl ester sulfonate surfactant, especially for laundry applications, comprise alkyl ester sulfonate surfactants of the structural formula:

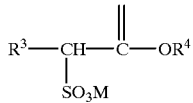

wherein $R^3$ is a $C_8$–$C_{20}$ hydrocarbyl, preferably an alkyl, or combination thereof, $R^4$ is a $C_1$–$C_6$ hydrocarbyl, preferably an alkyl, or combination thereof, and M is a cation which forms a water soluble salt with the alkyl ester sulfonate. Suitable salt-forming cations include metals such as sodium, potassium, and lithium, and substituted or unsubstituted ammonium cations, such as monoethanolamine, diethanolamine, and triethanolamine. Preferably, $R^3$ is $C_{10}$–$C_{16}$ alkyl, and $R^4$ is methyl, ethyl or isopropyl. Especially preferred are the methyl ester sulfonates wherein $R^3$ is $C_{10}$–$C_{16}$ alkyl.

Other suitable anionic surfactants include the alkyl sulfate surfactants which are water soluble salts or acids of the formula ROSO$_3$M wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g. sodium, potassium, lithium), or ammonium or substituted ammonium (e.g. methyl-, dimethyl-, and trimethyl ammonium cations and quaternary ammonium cations such as tetramethyl-ammonium and dimethyl piperdinium cations and quaternary ammonium cations derived from alkylamines such as ethylamine, diethylamine, triethylamine, and mixtures thereof, and the like). Typically, alkyl chains of $C_{12}$–$C_{16}$ are preferred for lower wash temperatures (e.g. below about 50° C.) and $C_{16-18}$ alkyl chains are preferred for higher wash temperatures (e.g. above about 50° C.).

Other anionic surfactants useful for detersive purposes can also be included in the laundry detergent compositions of the present invention. These can include salts (including, for example, sodium, potassium, ammonium, and substituted ammonium salts such as mono-, di- and triethanolamine salts) of soap, $C_8$–$C_{22}$ primary of secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl glycerol sulfonates, fatty acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$–$C_{18}$ monoesters) and diesters of sulfosuccinates (especially saturated and unsaturated $C_6$–$C_{12}$ diesters), acyl sarcosinates, sulfates of alkylpolysaccharides such as the sulfates of alkylpolyglucoside (the nonionic nonsulfated compounds being described below), branched primary alkyl sulfates, and alkyl polyethoxy carboxylates such as those of the formula RO($CH_2CH_2O)_k$—$CH_2COO$—M+ wherein R is a $C_8$–$C_{22}$ alkyl, k is an integer from 1 to 10, and M is a soluble salt-forming cation. Resin acids and hydrogenated resin acids are also suitable, such as rosin, hydrogenated rosin, and resin acids and hydrogenated resin acids present in or derived from tall oil.

Further examples are described in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23 (herein incorporated by reference).

When included therein, the laundry detergent compositions of the present invention typically comprise from about 1% to about 40%, preferably from about 3% to about 20% by weight of such anionic surfactants.

The laundry detergent compositions of the present invention may also contain cationic, ampholytic, zwitterionic, and semi-polar surfactants, as well as the nonionic and/or anionic surfactants other than those already described herein. Cationic detersive surfactants suitable for use in the laundry detergent compositions of the present invention are those having one long-chain hydrocarbyl group. Examples of such cationic surfactants include the ammonium surfactants such as alkyltrimethylammonium halogenides, and those surfactants having the formula:

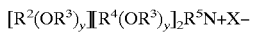

wherein $R^2$ is an alkyl or alkyl benzyl group having from about 8 to about 18 carbon atoms in the alkyl chain, each $R^3$ is selected from the group consisting of —$CH_2CH_2$—, —$CH_2CH(CH_3)$—, —$CH_2CH(CH_2OH)$—, —$CH_2CH_2CH_2$—, and mixtures thereof; each $R^4$ is selected from the group consisting of $C_1$–$C_4$ alkyl, $C_1$–$C_4$ hydroxyalkyl, benzyl ring structures formed by joining the two $R^4$ groups, —$CH_2CHOH$—CHOHCOR$^6$CHOHCH$_2$OH wherein $R^6$ is any hexose or hexose polymer having a molecular weight less than about 1000, and hydrogen when y is not 0; $R^5$ is the same as $R^4$ or is an alkyl chain wherein the total number of carbon atoms of $R^2$ plus $R^5$ is not more than about 18; each y is from 0 to about 10 and the sum of the y values is from 0 to about 15; and X is any compatible anion.

Highly preferred cationic surfactants are the water-soluble quaternary ammonium compounds useful in the present composition having the formula:

$$R_1R_2R_3R_4N+X-$$ (i)

wherein $R_1$ is $C_8$–$C_{16}$ alkyl, each of $R_2$, $R_3$ and $R_4$ is independently $C_1$–$C_4$ alkyl, $C_1$–$C_4$ hydroxy alkyl, benzyl, and —$(C_2H_{40})_x$H where x has a value from 2 to 5, and X is an anion. Not more than one of $R_2$, $R_3$ or $R_4$ should be benzyl. The preferred alkyl chain length for $R_1$ is $C_{12}$–$C_{15}$ particularly where the alkyl group is a mixture of chain lengths derived from coconut or palm kernel fat or is derived synthetically by olefin build up or OXO alcohols synthesis.

Preferred groups for $R_2R_3$ and $R_4$ are methyl and hydroxyethyl groups and the anion X may be selected from halide, methosulphate, acetate and phosphate ions. Examples of suitable quaternary ammonium compounds of formulae (i) for use herein are:

coconut trimethyl ammonium chloride or bromide;
coconut methyl dihydroxyethyl ammonium chloride or bromide;
decyl triethyl ammonium chloride;
decyl dimethyl hydroxyethyl ammonium chloride or bromide;
$C_{12-15}$ dimethyl hydroxyethyl ammonium chloride or bromide;
coconut dimethyl hydroxyethyl ammonium chloride or bromide;
myristyl trimethyl ammonium methyl sulphate;
lauryl dimethyl benzyl ammonium chloride or bromide;
lauryl dimethyl (ethenoxy)$_4$ ammonium chloride or bromide;
choline esters (compounds of formula (i) wherein $R_1$ is

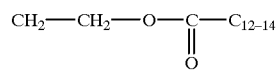

di-alkyl imidazolines [compounds of formula (i)].

Other cationic surfactants useful herein are also described in U.S. Pat. No. 4,228,044, Cambre, issued Oct. 14, 1980 and in European Patent Application EP 000,224.

When included therein, the laundry detergent compositions of the present invention typically comprise from 0.2% to about 25%, preferably from about 1% to about 8% by weight of such cationic surfactants.

Ampholytic surfactants are also suitable for use in the laundry detergent compositions of the present invention. These surfactants can be broadly described as aliphatic derivatives of secondary or tertiary amines, or aliphatic derivatives of heterocyclic secondary and tertiary amines in which the aliphatic radical can be straight- or branched-chain. One of the aliphatic substituents contains at least about 8 carbon atoms, typically from about 8 to about 18 carbon atoms, and at least one contains an anionic water-solubilizing group, e.g. carboxy, sulfonate, sulfate. See U.S. Pat. No. 3,929,678 to Laughlin et al., issued Dec. 30, 1975 at column 19, lines 18–35, for examples of ampholytic surfactants.

When included therein, the laundry detergent compositions of the present invention typically comprise from 0.2% to about 15%, preferably from about 1% to about 10% by weight of such ampholytic surfactants.

Zwitterionic surfactants are also suitable for use in laundry detergent compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 to Laughlin et al., issued Dec. 30, 1975 at column 19, line 38 through column 22, line 48, for examples of zwitterionic surfactants.

When included therein, the laundry detergent compositions of the present invention typically comprise from 0.2% to about 15%, preferably from about 1% to about 10% by weight of such zwitterionic surfactants.

Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula

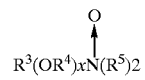

wherein $R^3$ is an alkyl hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3; and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxy ethyl amine oxides.

When included therein, the laundry detergent compositions of the present invention typically comprise from 0.2% to about 15%1 preferably from about 1% to about 10% by weight of such semi-polar nonionic surfactants.

Suitable detergent ingredients that can be added are enzyme oxidation scavengers which are described in Copending European Patent application 92870018.6 filed on Jan. 31, 1992. Examples of such enzyme oxidation scavengers are ethoxylated tetraethylene polyamines.

Especially preferred detergent ingredients are combinations with technologies which also provide a type of color care benefit. Examples of these technologies are metallo catalysts for color maintenance. Such metallo catalysts are described in copending European Patent Application No. 92870181.2.

Additional optional detergent ingredients that can be included in the detergent compositions of the pre sent invention include bleaching agents such as PB1, PB4 and percarbonate with a particle size of 400–800 microns. These bleaching agent components can include one or more oxygen bleaching agents and, depending upon the bleaching agent chosen, one or more bleach activators. When present oxygen bleaching compounds will typically be present at levels of from about 1% to about 25%. In general, bleaching compounds are optional components in non-liquid formulations, e.g. granular detergents.

The bleaching agent component for use herein can be any of the bleaching agents useful for detergent compositions including oxygen bleaches as well as others known in the art.

The bleaching agent suitable for the present invention can be an activated or non-activated bleaching agent.

One category of oxygen bleaching agent that can be used encompasses percarboxylic acid bleaching agents and salts thereof. Suitable examples of this class of agents include magnesium monoperoxyphthalate hexahydrate, the magnesium salt of meta-chloro perbenzoic acid, 4-nonylamino-4-oxoperoxybutyric acid and diperoxydode-canedioic acid. Such bleaching agents are disclosed in U.S. Pat. No. 4,483,781, U.S. patent application Ser. No. 740,446, European Patent Application 0,133,354 and U.S. Pat. No. 4,412,934. Highly preferred bleaching agents also include 6-nonylamino-6-oxoperoxycaproic acid as described in U.S. Pat. No. 4,634,551. Another category of bleaching agents that can be used encompasses the halogen bleaching agents. Examples of hypohalite bleaching agents, for example, include trichloro isocyanuric acid and the sodium and potassium dichloroisocyanurates and N-chloro and N-bromo alkane sulphonamides. Such materials are normally added at 0.5–10% by weight of the finished product, preferably 1–5% by weight.

The hydrogen peroxide releasing agents can be used in combination with bleach activators such as tetraacetylethylenediamine (TAED), nonanoyloxybenzene-sulfonate (NOBS, described in U.S. Pat. No. 4,412,934), 3,5,-trimethylhexanoloxybenzenesulfonate (ISONOBS, described in EP 120,591) or pentaacetylglucose (PAG), which are perhydrolyzed to form a peracid as the active bleaching species, leading to improved bleaching effect. In addition, very suitable are the bleach activators C8(6-octanamido-caproyl)oxybenzenesulfonate, C9(6-nonamido caproyl) oxybenzenesulfonate and C10(6-decanamido caproyl)oxybenzene sulfonate or mixtures thereof. Also suitable activators are acylated citrate esters such as disclosed in Copending European Patent Application No. 91870207.7.

Useful bleaching agents, including peroxyacids and bleaching systems comprising bleach activators and peroxygen bleaching compounds for use in cleaning compositions according to the invention are described in our co-pending application U.S. Ser. NO. 08/136,626.

The hydrogen peroxide may also be present by adding an enzymatic system (i.e. an enzyme and a substrate therefore) which is capable of generating hydrogen peroxide at the beginning or during the washing and/or rinsing process. Such enzymatic systems are disclosed in EP Patent Application 91202655.6 filed Oct. 9, 1991.

Bleaching agents other than oxygen bleaching agents are also known in the art and can be utilized herein. One type of non-oxygen bleaching agent of particular interest includes photoactivated bleaching agents such as the sulfonated zinc and/or aluminum phthalocyanines. These materials can be deposited upon the substrate during the washing process. Upon irradiation with light, in the presence of oxygen, such as by hanging clothes out to dry in the daylight, the sulfonated zinc phthalocyanine is activated and, consequently, the substrate is bleached. Preferred zinc phthalocyanine and a photoactivated bleaching process are described in U.S. Pat. No. 4,033,718. Typically, detergent compositions will contain about 0.025% to about 1.25%, by weight, of sulfonated zinc phthalocyanine.

The compositions according to the present invention may further comprise a builder system. Any conventional builder system is suitable for use herein including aluminosilicate materials, silicates, polycarboxylates and fatty acids, materials such as ethylenediamine tetraacetate, metal ion sequestrants such as aminopolyphosphonates, particularly ethylenediamine tetramethylene phosphonic acid and diethylene triamine pentamethylenephosphonic acid. Though less preferred for obvious environmental reasons, phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP.

Another suitable inorganic builder material is layered silicate, e.g. SKS-6 (Hoechst). SKS-6 is a crystalline layered silicate consisting of sodium silicate ($Na_2Si_2O_5$).

Suitable polycarboxylates containing one carboxy group include lactic acid, glycolic acid and ether derivatives thereof as disclosed in Belgian Patent Nos. 831,368, 821,369 and 821,370. Polycarboxylates containing two carboxy groups include the water-soluble salts of succinic acid, malonic acid, (ethylenedioxy) diacetic acid, maleic acid, diglycollic acid, tartaric acid, tartronic acid and fumaric acid, as well as the ether carboxylates described in German Offenlegenschrift 2,446,686, and 2,446,687 and U.S. Pat. No. 3,935,257 and the sulfinyl carboxylates described in Belgian Patent No. 840,623. Polycarboxylates containing three carboxy groups include, in particular, water-soluble citrates, aconitrates and citraconates as well as succinate derivatives such as the carboxymethyloxysuccinates described in British Patent No. 1,379,241, lactoxysuccinates described in Netherlands Application 7205873, and the oxypolycarboxylate materials such as 2-oxa-1,1,3-propane tricarboxylates described in British Patent No. 1,387,447.

Polycarboxylates containing four carboxy groups include oxydisuccinates disclosed in British Patent No. 1,261,829, 1,1,2,2-ethane tetracarboxylates, 1,1,3,3-propane tetracarboxylates and 1,1,2,3-propane tetracarboxylates. Polycarboxylates containing sulfo substituents include the sulfosuccinate derivatives disclosed in British Patent Nos. 1,398,421 and 1,398,422 and in U.S. Pat. No. 3,936,448, and the sulfonated pyrolysed citrates described in British Patent No. 1,082,179, while polycarboxylates containing phosphone substituents are disclosed in British Patent No. 1,439,000.

Alicyclic and heterocyclic polycarboxylates include cyclopentane-cis,cis, cis-tetracarboxylates, cyclopentadienide pentacarboxylates, 2,3,4,5-tetrahydro-furan—cis, cis, cis-tetracarboxylates, 2,5-tetrahydro-furan—cis—dicarboxylates, 2,2,5,5-tetrahydrofuran-tetracarboxylates, 1,2,3,4,5,6-hexane -hexacar-boxylates and and carboxymethyl derivatives of polyhydric alcohols such as sorbitol, mannitol and xylitol. Aromatic poly-carboxylates include mellitic acid, pyromellitic acid and the phthalic acid derivatives disclosed in British Patent No. 1,425,343.

Of the above, the preferred polycarboxylates are hydroxycarboxylates containing up to three carboxy groups per molecule, more particularly citrates.

Preferred builder systems for use in the present compositions include a mixture of a water-insoluble aluminosilicate builder such as zeolite A or of a layered silicate (SKS-6), and a water-soluble carboxylate chelating agent such as citric acid.

A suitable chelant for inclusion in the detergent compositions in accordance with the invention is ethylenediamine-N,N'-disuccinic acid (EDDS) or the alkali metal, alkaline earth metal, ammonium, or substituted ammonium salts thereof, or mixtures thereof. Preferred EDDS compounds are the free acid form and the sodium or magnesium salt thereof. Examples of such preferred sodium salts of EDDS include $Na_2EDDS$ and $Na_4EDDS$. Examples of such preferred magnesium salts of EDDS include MgEDDS and $Mg_2EDDS$. The magnesium salts are the most preferred for inclusion in compositions in accordance with the invention.

Preferred builder systems include a mixture of a water-insoluble aluminosilicate builder such as zeolite A, and a watersoluble carboxylate chelating agent such as citric acid.

Other builder materials that can form part of the builder system for use in granular compositions include inorganic materials such as alkali metal carbonates, bicarbonates, silicates, and organic materials such as the organic phosphonates, amino polyalkylene phosphonates and amino polycarboxylates.

Other suitable water-soluble organic salts are the homo- or co-polymeric acids or their salts, in which the polycarboxylic acid comprises at least two carboxyl radicals separated from each other by not more than two carbon atoms. Polymers of this type are disclosed in GB-A-1,596,756. Examples of such salts are polyacrylates of MW 2000–5000 and their copolymers with maleic anhydride, such copolymers having a molecular weight of from 20,000 to 70,000, especially about 40,000.

Detergency builder salts are normally included in amounts of from 10% to 80% by weight of the composition preferably from 20% to 70% and most usually from 30% to 60% by weight.

Another optional ingredient is a suds suppressor, exemplified by silicones, and silica-silicone mixtures. Silicones can be generally represented by alkylated polysiloxane materials while silica is normally used in finely divided forms exemplified by silica aerogels and xerogels and hydrophobic silicas of various types. These materials can be incorporated as particulates in which the suds suppressor is advantageously releasably incorporated in a water-soluble or water-dispersible, substantially non-surface-active detergent impermeable carrier. Alternatively the suds suppressor can be dissolved or dispersed in a liquid carrier and applied by spraying on to one or more of the other components.

A preferred silicone suds controlling agent is disclosed in Bartollota et al. U.S. Pat. No. 3,933,672. Other particularly useful suds suppressors are the self-emulsifying silicone suds suppressors, described in German Patent Application DTOS 2 646 126 published Apr. 28, 1977. An example of such a compound is DC-544, commercially available from Dow Corning, which is a siloxane-glycol copolymer. Especially preferred suds controlling agent are the suds suppressor system comprising a mixture of silicone oils and 2-alkyl-alcanols. Suitable 2-alkyl-alkanols are 2-butyl-octanol which are commercially available under the trade name Isofol 12 R.

Such suds suppressor system are described in Copending European Patent application N 92870174.7 filed Nov. 10, 1992.

Especially preferred silicone suds controlling agents are described in Copending European Patent application No 92201649.8. Said compositions can comprise a silicone/silica mixture in combination with fumed nonporous silica such as $Aerosil^R$.

The suds suppressors described above are normally employed at levels of from 0.001% to 2% by weight of the composition, preferably from 0.01% to 1% by weight.

Other components used in detergent compositions may be employed, such as soil-suspending agents, soil-release agents, optical brighteners, abrasives, bactericides, tarnish inhibitors, coloring agents, and/or encapsulated or non-encapsulated perfumes.

Especially suitable encapsulating materials are water soluble capsules which consist of a matrix of polysaccharide and polyhydroxy compounds such as described in GB 1,464,616.

Other suitable water soluble encapsulating materials comprise dextrins derived from ungelatinized starch acid-esters of substituted dicarboxylic acids such as described in U.S. Pat. No. 3,455,838. These acid-ester dextrins are,preferably, prepared from such starches as waxy maize, waxy sorghum, sago, tapioca and potato. Suitable examples of said encapsulating materials include N-Lok manufactured by National Starch. The N-Lok encapsulating material consists of a modified maize starch and glucose. The starch is modified by adding monofunctional substituted groups such as octenyl succinic acid anhydride.

Antiredeposition and soil suspension agents suitable herein include cellulose derivatives such as methylcellulose, carboxymethylcellulose and hydroxyethylcellulose, and homo- or co-polymeric polycarboxylic acids or their salts. Polymers of this type include the polyacrylates and maleic anhydride-acrylic acid copolymers previously mentioned as builders, as well as copolymers of maleic anhydride with ethylene, methylvinyl ether or methacrylic acid, the maleic anhydride constituting at least 20 mole percent of the copolymer. These materials are normally used at levels of from 0.5% to 10% by weight, more preferably from 0.75% to 8%, most preferably from 1% to 6% by weight of the composition.

Preferred optical brighteners are anionic in character, examples of which are disodium 4,4'-bis-(2-diethanolamino-4-anilino-s-triazin-6-ylamino)stilbene-2:2' disulphonate, disodium 4,-4'-bis-(2-morpholino-4-anilino-s-triazin-6-ylamino-stilbene-2:2'-disulphonate, disodium 4,4'-bis-(2,4-dianilino-s-triazin-6-ylamino)stilbene-2:2' disulphonate, monosodium 4', 41'-bis-(2,4-dianilino-s-tri-azin-6 ylamino) stilbene-2-sulphonate, disodium 4,4'-bis-(2-anilino-4-(N-methyl-N-2-hydroxyethylamino)-s-triazin-6-ylamino) stilbene-2,2'-disulphonate, di-sodium 4,4'-bis-(4-phenyl-2, 1,3-triazol-2-yl)-stilbene-2,2' disulphonate, di-so-dium 4,4' bis(2-anilino-4-(1-methyl-2-hydroxyethylamino)-s-triazin-6-ylami-no)stilbene-2,2' disulphonate, sodium 2(stilbyl-4"-(naphtho-1',2',:4,5)-1,2,3-triazole-2"-sulphonate and 4,4'-bis (2-sulphostyryl)biphenyl.

Other useful polymeric materials are the polyethylene glycols, particularly those of molecular weight 1000–10000, more particularly 2000 to 8000 and most preferably about 4000. These are used at levels of from 0.20% to 5% more preferably from 0.25% to 2.5% by weight. These polymers and the previously mentioned homo- or co-polymeric polycarboxylate salts are valuable for improving whiteness maintenance, fabric ash deposition, and cleaning performance on clay, proteinaceous and oxidizable soils in the presence of transition metal impurities.

Soil release agents useful in compositions of the present invention are conventionally copolymers or terpolymers of terephthalic acid with ethylene glycol and/or propylene glycol units in various arrangements. Examples of such polymers are disclosed in the commonly assigned U.S. Pat. Nos. 4116885 and 4711730 and European Published Patent Application No. 0 272 033. A particular preferred polymer in accordance with EP-A-0 272 033 has the formula

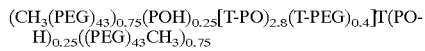
(CH$_3$(PEG)$_{43}$)$_{0.75}$(POH)$_{0.25}$[T-PO)$_{2.8}$(T-PEG)$_{0.4}$]T(PO-H)$_{0.25}$((PEG)$_{43}$CH$_3$)$_{0.75}$ where PEG is —(OC$_2$H$_4$)O—, PO is (OC$_3$H$_6$O) and T is (pcOC$_6$H$_4$CO).

Also very useful are modified polyesters as random copolymers of dimethyl terephthalate, dimethyl sulfoisophthalate, ethylene glycol and 1–2 propane diol, the end groups consisting primarily of sulphobenzoate and secondarily of mono esters of ethylene glycol and/or propane-diol. The target is to obtain a polymer capped at both end by sulphobenzoate groups, "primarily", in the present context most of said copolymers herein will be end-capped by sulphobenzoate groups. However, some copolymers will be less than fully capped, and therefore their end groups may consist of monoester of ethylene glycol and/or propane 1–2 diol, thereof consist "secondarily" of such species.

The selected polyesters herein contain about 46% by weight of dimethyl terephthalic acid, about 16% by weight of propane -1.2 diol, about 10% by weight ethylene glycol about 13% by weight of dimethyl sulfobenzoic acid and about 15% by weight of sulfoisophthalic acid, and have a molecular weight of about 3.000. The polyesters and their method of preparation are described in detail in EPA 311 342.

Softening Agents

Fabric softening agents can also be incorporated into laundry detergent compositions in accordance with the present invention. These agents may be inorganic or organic in type. Inorganic softening agents are exemplified by the smectite clays disclosed in GB-A-1 400 898 and in U.S. Pat. No. 5,019,292. Organic fabric softening agents include the water insoluble tertiary amines as disclosed in GB-A1 514 276 and EP-B0 011 340 and their combination with mono C12–C14 quaternary ammonium salts are disclosed in EP-B-0 026 527 and EP-B-0 026 528 and di-long-chain amides as disclosed in EP-B-0 242 919. Other useful organic ingredients of fabric softening systems include high molecular weight polyethylene oxide materials as disclosed in EP-A-0 299 575 and 0 313 146.

Levels of smectite clay are normally in the range from 5% to 15%, more preferably from 8% to 12% by weight, with the material being added as a dry mixed component to the remainder of the formulation. Organic fabric softening agents such as the water-insoluble tertiary amines or dilong chain amide materials are incorporated at levels of from 0.5% to 5% by weight, normally from 1% to 3% by weight whilst the high molecular weight polyethylene oxide materials and the water soluble cationic materials are added at levels of from 0.1% to 2%, normally from 0.15% to 1.5% by weight. These materials are normally added to the spray dried portion of the composition, although in some instances it may be more convenient to add them as a dry mixed particulate, or spray them as molten liquid on to other solid components of the composition.

Dye Transfer Inhibition

The present invention also relates to a process for inhibiting dye transfer from one fabric to another of solubilized and suspended dyes encountered during fabric laundering operations involving colored fabrics.

Polymeric Dye Transfer Inhibiting Agents

The detergent compositions according to the present invention also comprise from 0.001% to 10%, preferably from 0.01% to 2%, more preferably from 0.05% to 1% by weight of polymeric dye transfer inhibiting agents. Said polymeric dye transfer inhibiting agents are normally incorporated into detergent compositions in order to inhibit the transfer of dyes from colored fabrics onto fabrics washed therewith. These polymers have the ability to complex or adsorb the fugitive dyes washed out of dyed fabrics before the dyes have the opportunity to become attached to other articles in the wash.

Especially suitable polymeric dye transfer inhibiting agents are polyamine N-oxide polymers, copolymers of N-vinylpyrrolidone and N-vinylimidazole, polyvinylpyrrolidone polymers, polyvinyloxazolidones and polyvinylimidazoles or mixtures thereof.

Addition of such polymers also enhances the performance of the enzymes according the invention.

a) Polyamine N-oxide Polymers

The polyamine N-oxide polymers suitable for use contain units having the following structure formula:

(I)

wherein P is a polymerisable unit, whereto the R—N—O group can be attached to or wherein the R—N—O group forms part of the polymerisable unit or a combination of both.

A is

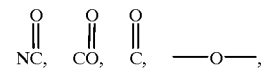

—S—, —N—, x is 0 or 1; R are aliphatic, ethexylated aliphatics, aromatic, heterocyclic or alicyclic groups or any combination thereof whereto the nitrogen of the N—O group can be attached or wherein the nitrogen of the N—O group is part of these groups.

The N—O group can be represented by the following general structures:

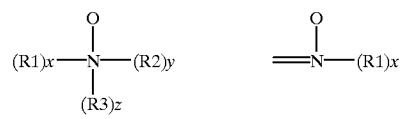

wherein R1, R2, and R3 are aliphatic groups, aromatic, heterocyclic or alicyclic groups or combinations thereof, x or/and y or/and z is 0 or 1 and wherein the nitrogen of the N—O group can be attached or wherein the nitrogen of the N—O group forms part of these groups.

The N—O group can be part of the polymerisable unit (P) or can be attached to the polymeric backbone or a combination of both.

Suitable polyamine N-oxides wherein the N—O group forms part of the polymerisable unit comprise polyamine N-oxides wherein R is selected from aliphatic, aromatic, alicyclic or heterocyclic groups.

One class of said polyamine N-oxides comprises the group of polyamine N-oxides wherein the nitrogen of the N—O group forms part of the R-group. Preferred polyamine N-oxides are those wherein R is a heterocyclic group such as pyrridine, pyrrole, imidazole, pyrrolidine, piperidine, quinoline, acridine and derivatives thereof.

Another class of said polyamine N-oxides comprises the group of polyamine N-oxides wherein the nitrogen of the N—O group is attached to the R-group.

Other suitable polyamine N-oxides are the polyamine oxides whereto the N—O group is attached to the polymerisable unit.

Preferred class of these polyamine N-oxides are the polyamine N-oxides having the general formula (I) wherein R is an aromatic, heterocyclic or alicyclic groups wherein the nitrogen of the N—O functional group is part of said R group.

Examples of these classes are polyamine oxides wherein R is a heterocyclic compound such as pyrridine, pyrrole, imidazole and derivatives thereof.

Another preferred class of polyamine N-oxides are the polyamine oxides having the general formula (I) wherein R are aromatic, heterocyclic or alicyclic groups wherein the nitrogen of the N—O functional group is attached to said R groups.

Examples of these classes are polyamine oxides wherein R groups can be aromatic such as phenyl.

Any polymer backbone can be used as long as the amine oxide polymer formed is water-soluble and has dye transfer inhibiting properties. Examples of suitable polymeric backbones are polyvinyls, polyalkylenes, polyesters, polyethers, polyamide, polyimides, polyacrylates and mixtures thereof.

The amine N-oxide polymers of the present invention typically have a ratio of amine to the amine N-oxide of 10:1 to 1:1000000. However the amount of amine oxide groups present in the polyamine oxide polymer can be varied by appropriate copolymerization or by appropriate degree of N-oxidation. Preferably, the ratio of amine to amine N-oxide is from 2:3 to 1:1000000. More preferably from 1:4 to 1:1000000, most preferably from 1:7 to 1:1000000. The polymers of the present invention actually encompass random or block copolymers where one monomer type is an amine N-oxide and the other monomer type is either an amine N-oxide or not. The amine oxide unit of the polyamine N-oxides has a PKa <10, preferably PKa <7, more preferred PKa <6.

The polyamine oxides can be obtained in almost any degree of polymerisation. The degree of polymerisation is not critical provided the material has the desired water-solubility and dye-suspending power.

Typically, the average molecular weight is within the range of 500 to 1000,000; preferably from 1,000 to 50,000, more preferably from 2,000 to 30,000, most preferably from 3,000 to 20,000.

b) Copolymers of N-vinylpyrrolidone and N-vinylimidazole

The N-vinylimidazole N-vinylpyrrolidone polymers used in the present invention have an average molecular weight range from 5,000–1,000,000, preferably from 20,000–200,000.

Highly preferred polymers for use in detergent compositions according to the present invention comprise a polymer selected from N-vinylimidazole N-vinylpyrrolidone copolymers wherein said polymer has an average molecular weight range from 5,000 to 50,000 more preferably from 8,000 to 30,000, most preferably from 10,000 to 20,000.

The average molecular weight range was determined by light scattering as described in Barth H. G. and Mays J. W. Chemical Analysis Vol 113, "Modern Methods of Polymer Characterization".

Highly preferred N-vinylimidazole N-vinylpyrrolidone copolymers have an average molecular weight range from 5,000 to 50,000; more preferably from 8,000 to 30,000; most preferably from 10,000 to 20,000.

The N-vinylimidazole N-vinylpyrrolidone copolymers characterized by having said average molecular weight range provide excellent dye transfer inhibiting properties while not adversely affecting the cleaning performance of detergent compositions formulated therewith.

The N-vinylimidazole N-vinylpyrrolidone copolymer of the present invention has a molar ratio of N-vinylimidazole to N-vinylpyrrolidone from 1 to 0.2, more preferably from 0.8 to 0.3, most preferably from 0.6 to 0.4.

c) Polyvinylpyrrolidone

The detergent compositions of the present invention may also utilize polyvinylpyrrolidone ("PVP") having an average molecular weight of from about 2,500 to about 400,000, preferably from about 5,000 to about 200,000, more preferably from about 5,000 to about 50,000, and most preferably from about 5,000 to about 15,000. Suitable polyvinylpyrrolidones are commercially vailable from ISP Corporation, New York, N.Y. and Montreal, Canada under the product names PVP K-15 (viscosity molecular weight of 10,000), PVP K-30 (average molecular weight of 40,000), PVP K-60 (average molecular weight of 160,000), and PVP K-90 (average molecular weight of 360,000). Other suitable polyvinylpyrrolidones which are commercially available from BASF Cooperation include Sokalan HP 165 and Sokalan HP 12; polyvinylpyrrolidones known to persons skilled in the detergent field (see for example EP-A-262,897 and EP-A-256,696).

d) Polyvinyloxazolidone:

The detergent compositions of the present invention may also utilize polyvinyloxazolidone as a polymeric dye transfer inhibiting agent. Said polyvinyloxazolidones have an average molecular weight of from about 2,500 to about 400,000, preferably from about 5,000 to about 200,000, more preferably from about 5,000 to about 50,000, and most preferably from about 5,000 to about 15,000.

e) Polyvinylimidazole:

The detergent compositions of the present invention may also utilize polyvinylimidazole as polymeric dye transfer inhibiting agent. Said polyvinylimidazoles have an average about 2,500 to about 400,000, preferably from about 5,000 to about 200,000, more preferably from about 5,000 to about 50,000, and most preferably from about 5,000 to about 15,000.

Method of washing

The process described herein comprises contacting fabrics with a laundering solution in the usual manner and exemplified hereunder.

The process of the invention is conveniently carried out in the course of the cleaning process. The method of cleaning is preferably carried out at 5° C. to 95° C., especially between 10° C. and 60° C. The pH of the treatment solution is preferably from 7 to 11, especially from 7.5 to 10.5.

The following examples are meant to exemplify compositions of the present invention, but are not necessarily meant to limit or otherwise define the scope of the invention.

In the detergent compositions, the abbreviated component identifications have the following meanings:

LAS: Sodium linear $C_{12}$ alkyl benzene sulphonate

TAS: Sodium tallow alkyl sulphate

XYAS: Sodium $C_{1X}$–$C_{1Y}$ alkyl sulfate

SAS: $C_{12}$–$C_{14}$ secondary (2,3) alkyl sulfate in the form of the sodium salt.

APG: Alkyl polyglycoside surfactant of formula $C_{12}$-(glycosyl)$_x$, where x is AEC: Alkyl ethoxycarboxylate surfactant of formula $C_{12}$ ethoxy (2) carboxylate.

SS: Secondary soap surfactant of formula 2-butyl octanoic acid

25EY: A $C_{12}$–$C_{15}$ predominantly linear primary alcohol condensed with an average of Y moles of ethylene oxide 45EY: A $C_{14}-C_{15}$ predominantly linear primary alcohol condensed with an average of Y moles of ethylene oxide XYEZS: $C_{1X}-C_{1Y}$ sodium alkyl sulfate condensed with an average of Z moles of ethylene oxide per mole Nonionic: $C_{13}-C_{15}$ mixed ethoxylated/propoxylated fatty alcohol with an average degree of ethoxylation of 3.8 and an average degree of propoxylation of 4.5 sold under the tradename Plurafax LF404 by BASF Gmbh CFAA: $C_{12}-C_{14}$ alkyl N-methyl glucamide TFAA: $C_{16}-C_{18}$ alkyl N-methyl glucamide.

Silicate: Amorphous Sodium Silicate ($SiO_2:Na_2O$ ratio=2.0)

NaSKS-6: Crystalline layered silicate of formula $\delta-Na_2Si_2O_5$

Carbonate: Anhydrous sodium carbonate

Phosphate: Sodium tripolyphosphate

MA/AA: Copolymer of 1:4 maleic/acrylic acid, average molecular weight about 80,000

Polyacrylate: Polyacrylate homopolymer with an average molecular weight of 8,000 sold under the tradename PA30 by BASF GmbH Zeolite A: Hydrated Sodium Aluminosilicate of formula $Na_{12}(AlO_2SiO_2)_{12} \cdot 27H_2O$ having a primary particle size in the range from 1 to 10 micrometers Citrate: Tri-sodium citrate dihydrate Citric: Citric Acid Perborate: Anhydrous sodium perborate monohydrate bleach, empirical formula $NaBO_2.H_2O_2$ PB4: Anhydrous sodium perborate tetrahydrate Percarbonate: Anhydrous sodium percarbonate bleach of empirical formula $2Na_2CO_3.3H_2O_2$ TAED: Tetraacetyl ethylene diamine Paraffin: Paraffin oil sold under the tradename Winog 70 by Wintershall.

Protease: Proteolytic enzyme sold under the tradename Savinase by Novo Nordisk A/S.

Amylase: Amylolytic enzyme sold under the tradename Termamyl by Novo Nordisk A/S Lipase: Lipolytic enzyme sold under the tradename Lipolase by Novo Nordisk A/S Peroxidase: Peroxidase enzyme CMC: Sodium carboxymethyl cellulose HEDP: 1,1-hydroxyethane diphosphonic acid DETPMP: Diethylene triamine penta (methylene phosphonic acid), marketed by Monsanto under the Trade name Dequest 2060

PVP: Polyvinyl pyrrolidone polymer

EDDS: Ethylenediamine-N, N'-disuccinic acid, [S,S] isomer in the form of the sodium salt.

Suds Suppressor: 25% paraffin wax Mpt 50° C., 17% hydrophobic silica, 58% paraffin oil.

Granular Suds Suppressor: 12% Silicone/silica, 18% stearyl alcohol, 70% starch in granular form SCS: Sodium cumene sulphonate Sulphate: Anhydrous sodium sulphate.

HMWPEO: High molecular weight polyethylene oxide

PGMS: Polyglycerol monostearate having a tradename of Radiasurf 248

TAE 25: Tallow alcohol ethoxylate (25)

EXAMPLES

Example 1

Endoglucanase has been immobilized on polyethylene glycol with molecular weight 5000 via the cyanogen chloride activation step and at different weight ratio polymer to endoglucanase. At a 13/1 molar ratio the enzyme-PEG 5000 compound has been characterized as a mixture of compounds with one or more polymer molecules immobilized to the endoglucanase (SDS-PAGE) At the molar ratio 1/2 predominantly intra-molecular bounds are formed between two or more endoglucanase structures.

The stressed storage stability of this immobilized endoglucanase in a heavy duty liquid detergent with protease is improved versus the stability of the free endoglucanase. On an equal protein basis the endoglucanase depilling performance is at >70% and the tensile strength loss is reduced with more then 30% versus the free enzyme.

The enzyme(s) immobilized by a covalent binding on an activated polymer are added to the following exemplifying detergent and/or fabric softener compositions.

Endoglucanase: 43 kd endoglucanase derived from Humicola insolens DSM 1800.

Example 2

A compact granular fabric cleaning composition in accord with the invention was prepared as follows:

| | |
|---|---|
| 45AS | 8.0 |
| 25E3S | 2.0 |
| 25E5 | 3.0 |
| 25E3 | 3.0 |
| TFAA | 2.5 |
| Zeolite A | 17.0 |
| NaSKS-6 | 12.0 |
| Citric acid | 3.0 |
| Carbonate | 7.0 |
| MA/AA | 5.0 |
| CMC | 0.4 |
| Poly (4-vinylpyridine) -N-oxide/copolymer of vinylimidazole and vinylpyrrolidone | 0.2 |
| TAED | 6.0 |
| Percarbonate | 22.0 |
| EDDS | 0.3 |
| Granular suds suppressor | 3.5 |
| water/minors | Up to 100% |

Example 3

A granular fabric cleaning compositions in accord with the invention which provide "softening through the wash" capability were prepared as follows:

| | | |
|---|---|---|
| 45AS | — | 10.0 |
| LAS | 7.6 | — |
| 68AS | 1.3 | — |
| 45E7 | 4.0 | — |
| 25E3 | — | 5.0 |
| Coco-alkyl-dimethyl hydroxy-ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| Perborate | 15.0 | — |
| Percarbonate | — | 15.0 |
| TAED | 5.0 | 5.0 |
| Smectite clay | 10.0 | 10.0 |
| HMWPEO | — | 0.1 |
| Silicate | 3.0 | 5.0 |
| Carbonate | 10.0 | 10.0 |
| Granular suds suppressor | 1.0 | 4.0 |
| CMC | 0.2 | 0.1 |
| Water/minors | Up to 100% | |

Example 4

Heavy duty liquid fabric cleaning compositions suitable for use in the pretreatment of stained fabrics, and for use in a machine laundering method, in accord with the invention were prepared as follows:

|  | I | II | III | IV | V |
|---|---|---|---|---|---|
| 24AS | 20.0 | 20.0 | 20.0 | 20.0 | 20.0 |
| SS | 5.0 | 5.0 | 5.0 | 5.0 | 5.0 |
| Citrate | 1.0 | 1.0 | 1.0 | 1.0 | 1.0 |
| 12E$_3$ | 13.0 | 13.0 | 13.0 | 13.0 | 13.0 |
| Monethanolamine | 2.5 | 2.5 | 2.5 | 2.5 | 2.5 |
| Water/propylene glycol/ethanol (100:1:1) | | | | | |

Example 5

Heavy duty liquid fabric cleaning compositions in accord with the invention were prepared as follows:

|  | I | II | III | IV |
|---|---|---|---|---|
| LAS acid form | — | — | 25.0 | — |
| C$_{12-14}$ alkenyl succinic acid | 3.0 | 8.0 | 10.0 | — |
| Citric acid | 10.0 | 15.0 | 2.0 | 2.0 |
| 25AS acid form | 8.0 | 8.0 | — | 15.0 |
| 25AE2S acid form | — | 3.0 | — | 4.0 |
| 25AE7 | — | 8.0 | — | 6.0 |
| 25AE3 | 8.0 | — | — | — |
| CFAA | — | — | — | 6.0 |
| DETPMP | 0.2 | — | 1.0 | 1.0 |
| Fatty acid | — | — | — | 10.0 |
| Oleic acid | 1.8 | — | 1.0 | — |
| Ethanol | 4.0 | 4.0 | 6.0 | 2.0 |
| Propanediol | 2.0 | 2.0 | 6.0 | 10.0 |
| Coco-alkyl dimethyl hydroxy ethyl ammonium chloride | — | — | 3.0 | — |
| Smectite clay | — | — | 5.0 | — |
| PVP | 1.0 | 2.0 | — | — |
| Perborate | — | 1.0 | — | — |
| Phenol sulphonate | — | 0.2 | — | — |
| Peroxidase | — | 0.01 | — | — |
| NaOH | | Up to pH 7.5 | | |
| Waters/minors | | Up to 100% | | |

Example 6

The following rinse added fabric softener composition, in accord with the invention, was prepared (parts by weight).

| Softener active | 24.5 |
|---|---|
| PGMS | 2.0 |
| TAE 25 | 1.5 |
| HCL | 0.12 |
| Antifoam agent | 0.019 |
| Blue dye | 80 ppm |
| CaCl$_2$ | 0.35 |
| Perfume | 0.90 |

We claim:

1. A detergent composition comprising a surfactant and:
   a) from 0.0001% to 2%, by weight of the detergent composition, of one or more enzymes; and
   b) an activated polymer, wherein the polymer has a water soluble it of at least about $7.10^{-10}$ Mol/l;
      wherein each enzyme is immobilized by a covalent binding on the activated polymer and wherein the covalently bound polymer-enzyme does not release more than 5% of any of the starting components of the modified enzyme when exposed to a diluted wash solution of up to pH 11, at a solution temperature up to 90° C. and for at least 30 minutes.

2. A detergent composition according to claim 1 wherein the enzyme is covalently bound on an activated polymer via a spacer molecule.

3. A detergent composition according to claim 2 wherein the immobilization is a single-point or multi-point immobilization.

4. A detergent composition according to claim 3 wherein the molar ratio of activated polymer to enzyme is from 0.5:1 to 100:1.

5. A detergent composition according to claim 4 wherein the enzyme is selected from the group consisting of cellulases, hemicellulases, peroxidases, proteases, glucoamylases, amylases, lipases, cutinases, pectinases, reductases, oxidases, phenoloxidases, lipoxygenases, laccases, ligninases, pullulanases, xylanases, tannases, pentosanases, malanases, β-glucanases, arabinosidases, and mixtures thereof.

6. Detergent composition according to claim 5 wherein the cellulase enzyme consists essentially of a homogeneous endoglucanase component which is immunoreactive with an antibody raised against a highly purified 43 kD cellulose derived from Humicola insolens, DSM 1800, or which is homologous to said 43 kD endoglucanase.

7. A detergent composition according to claim 5 wherein the polymer is selected from the group consisting of polyvinylalcohol, polyvinylpyrrolidone, polyacrylamides, polyacrylate, alpha-hydroxy polyacrylate, polyamine N-oxide polymers, copolymers of N-vinylpyrrolidone and N-vinylimidazole, copolymers of N-vinylpyrrolidone and polyvinyloxa zolidones, copolymers of N-vinylpyrrolidone and polyvinylimidazoles, copolymers of polyvinylalcohol and polyvinylpyrrolidone, polyethylene glycol, block polymers of ethylene oxide and propylene oxide, polysaccharide, cellulose, substituted cellulose, cyclodextrin, dextran, agarose, proteins, collagen, polyaspartate and mixtures thereof.

8. A detergent composition according to claim 7 wherein the composition is a granular detergent composition containing no more than 15% by weight of inorganic filler salt.

9. A detergent composition according to claim 8 wherein the composition is a heavy duty liquid composition.

10. A fabric softening composition comprising a softening agent and:
    a) from 0.0001% to 2%, by weight of the fabric softening composition, of one or more enzymes; and
    b) an activated polymer; wherein the polymer has a water solubility of at least about $7.10^{-10}$ Mol/l;
       wherein each enzyme is immobilized by a covalent binding on the activated polymer, and wherein the covalently bound polymer-enzyme does not release more than 5% of any of the starting components of the modified enzyme when exposed to a diluted wash solution of up to pH 11, at a solution temperature up to 90° C. and for at least 30 minutes.

11. A detergent composition according to claim 7 wherein the enzyme is a protease.

12. A detergent composition according to claim 11 wherein the polymer is polyethylene glycol.

13. A detergent composition according to claim 12 wherein the molecular weight of the polymer is from about 0.5 kD to about 5000 kD.

14. A detergent composition according to claim 13 wherein the molecular weight of the polymer is from about 5 kD to about 20 kD.

15. A method of cleansing a substrate comprising contacting the substrate with a detergent composition according to claim 1.

16. A method according to claim 15 wherein the substrate is a fabric.

17. A method according to claim 15 wherein the substrate is a hard surface.

* * * * *